United States Patent
Fox et al.

(10) Patent No.: US 8,759,069 B2
(45) Date of Patent: *Jun. 24, 2014

(54) CONTAMINANT CONTROL IN ZYMOMONAS FERMENTATION USING HOP ACIDS

(75) Inventors: George C Fox, Wilmington, DE (US); Maria C Leana, Hockessin, DE (US); Brian G Lefebvre, Wilmington, DE (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/524,277

(22) Filed: Jun. 15, 2012

(65) Prior Publication Data

US 2013/0337520 A1 Dec. 19, 2013

(51) Int. Cl.
*C12N 1/20* (2006.01)
*C12P 7/06* (2006.01)

(52) U.S. Cl.
USPC ........................................ 435/252.1; 435/161

(58) Field of Classification Search
None
See application file for complete search history.

(56) References Cited

U.S. PATENT DOCUMENTS

| | | | |
|---|---|---|---|
| 5,514,583 A | 5/1996 | Picataggio et al. | |
| 5,843,760 A | 12/1998 | Zhang et al. | |
| 6,566,107 B1 | 5/2003 | Zhang | |
| 7,629,156 B2 | 12/2009 | Viitanen et al. | |
| 7,741,119 B2 | 6/2010 | Viitanen et al. | |
| 7,897,396 B2 | 3/2011 | Caimi et al. | |
| 7,989,206 B2 | 8/2011 | Viitanen et al. | |
| 7,998,722 B2 | 8/2011 | Viitanen et al. | |
| 2003/0016227 A1 | 1/2003 | Matthies | |
| 2004/0044087 A1 | 3/2004 | Maye | |
| 2009/0042276 A1 | 2/2009 | Maye | |
| 2011/0014670 A1 | 1/2011 | Caimi et al. | |
| 2011/0043408 A1 | 2/2011 | Shi et al. | |
| 2011/0318801 A1 | 12/2011 | Kahsay et al. | |
| 2012/0156746 A1 | 6/2012 | Caimi et al. | |

FOREIGN PATENT DOCUMENTS

| | | | | |
|---|---|---|---|---|
| WO | 2004072291 A2 | 8/2004 | | |
| WO | 2007145857 A1 | 12/2007 | | |
| WO | WO2010/096673 | * | 8/2010 | ............... C12N 1/00 |

OTHER PUBLICATIONS

Caballero et al., Importance of tetrahydroiso [alpha]-acids to the microbiological stability of beer, Journal of AOAC International, vol. 92, Issue 4 (Jul. 2009-Aug. 2009): 1160(5).*

Agrawal, Renu et al., Role of Antimicrobial Agents in Simultaneous Saccharification and Fermentation of Paddy Malt Mash to Ethanol by Mixed Cultures of *Saccharomyces cervisiae* PH03 and *Zymomonas mobilis* ZM4, Biotechnology Letters, Jun. 1996, pp. 673-678, vol. 18, No. 6.

Bischoff, Kenneth M. et al., Modeling Bacterial Contamination of Fuel Ethanol Fermentation, Biotechnology and Bioengineering, May 1, 2009, pp. 117-122, vol. 103, No. 1.

Day, W. H. et al., Antibiotics as Contamination-Control Agents in Grain Alcohol Fermentations, Agricultural and Food Chemistry, Mar. 3, 1954, pp. 252-258, vol. 2, No. 5.

(Continued)

*Primary Examiner* — Karen Cochrane Carlson
*Assistant Examiner* — Jennifer M. H. Tichy

(57) ABSTRACT

Contamination was controlled in fermentations using *Zymomonas mobilis* as the biocatalyst, without negative impact on fermentation production, by the addition of hop acids. The effective concentration of hop acids was found to be dependent upon the type of fermentation medium used.

5 Claims, 10 Drawing Sheets

(56) References Cited

OTHER PUBLICATIONS

Hynes, S. H. et al., Use of virginiamycin to control the growth of lactic acid bacteria during alcohol fermentation, Journal of Industrial Microbiology & Biotechnology, 1997, pp. 284-291, vol. 18.

Mohagheghi, Ali et al., Performance of a newly developed integrant of *Zymomonas mobilis* for ethanol production on corn stover hydrolysate, Biotechnology Letters, 2004, pp. 321-325, vol. 26.

Ruckle, L. et al., Hop acids can efficiently replace antibiotics in ethanol production, International Sugar Journal, 2006, pp. 139-147, vol. 108.

Swings, J. et al., The Biology of *Zymomonas*, Bacteriological Reviews, Mar. 1977, pp. 1-46, vol. 41, No. 1.

Walia, S. K. et al., Self-Transmissible Plasmid in *Zymomonas mobilis* Carrying Antibiotc Resistance, Jan. 1984, pp. 198-200, vol. 47, No. 1.

Grote, W. et al., The Susceptibility of Contamination of a *Zymomonas mobilis* Process for Ethanol Production, Journal of Fermentation Technology, 1985, pp. 287-290, vol. 63, No. 3.

Simpson, W. J., Ionophoric action of trans-isohumulone on *Lactobacillus brevis*, Journal of General Microbiology, 1993, pp. 1041-1045, vol. 139.

Agrawal, Renu et al., Fermentation of Paddy Malt Mash to Ethanol by Mixed Cultures of *Saccharomyces cerevisiae* and *Zymomonas mobilis* ZM4 with Penicillin G, Journal of Fermentation and Bioengineering, 1994, pp. 218-220, vol. 77, No. 2.

Muthaiyan, Arunachalam et al., Antimicrobial strategies for limiting bacterial contaminants in fuel bioethanol fermentations, Progress in Energy and Combustion Science, 2011, pp. 351-370, vol. 37.

International Search Report dated Aug. 26, 2013, International Application No. PCT/US2013/044926.

* cited by examiner

CONTAMINANT CONTROL IN *ZYMOMONAS* FERMENTATION USING HOP ACIDS

FIELD OF THE INVENTION

The invention relates to the fields of microbiology and fermentation. More specifically, methods were developed for controlling contaminants of fermentations when *Zymomonas* is used as the biocatalyst.

BACKGROUND OF THE INVENTION

Fuel ethanol produced from renewable resources is one of the long-term solutions to global fossil fuel shortages, rising energy costs, and global warming effects related to increased atmospheric carbon dioxide. Fuel ethanol from renewable resources is produced by fermentation of sugars using a biocatalyst. Currently yeast is the biocatalyst most widely used for ethanol production. Fermentable sugars are most typically obtained from processed biomaterials including corn grain, sugarbeets, and sugarcane. An alternative abundant biomaterial sugar source is cellulosic or lignocellulosic biomass. Methods are being developed for processing of cellulosic and lignocellulosic biomass to produce fermentable sugars using physical, chemical, and/or enzymatic treatments.

It is difficult to maintain sterility in a large scale fermentation process, particularly when biomaterial is used as a carbohydrate source. Large scale fermentation processes are typically contaminated with bacteria that may come from the processed biomaterial, equipment, process water or other sources. Typically contaminating bacteria are lactic acid bacteria (LAB) such as *Lactobacillus* species. Contaminating bacteria reduce fermentation product yield by utilizing sugars and reducing effectiveness of the primary product biocatalyst. Contaminating bacteria produce undesired products such as acetic and lactic acid which increase stress conditions in a culture leading to poorer growth and/or production of the biocatalyst product.

Contaminating bacteria, predominantly lactic acid bacteria, have been a problem in yeast fermentations, typically of mash or molasses, for ethanol production for either fuel or brewing. Due to differential sensitivities of yeast and contaminating bacteria to some antimicrobials, a number of antimicrobials can be used to control bacteria in yeast fermentations. Antimicrobials successfully used in yeast fermentations to control LAB contamination include penicillin (Day et al. (1954) Agricultural and Food Chemistry 2:252-258), virginiamycin (Hynes et al. (1997) J. of Industrial Microbiology & Biotechnology 18:284-291; Bischoff et al. (2009) Biotechnology and Bioengineering 103:117-122; WO2007145857), hop acids (US20040044087; Ruckle and Senn, (2006) International Sugar Journal 108:139-147), FermaSure™, as well as erythromycin, tylosin, and tetracycline.

*Zymomonas* is being developed as an effective biocatalyst for producing ethanol by engineering strain improvements including utilization of xylose and arabinose in addition to glucose, and inactivating competing metabolic pathways. In addition, *Zymomonas* has been adapted for use in hydrolysate fermentation medium by increasing tolerance to inhibitors present in biomass hydrolysate. However, using *Zymomonas* as a biocatalyst for ethanol fermentation presents additional challenges in contamination control since this biocatalyst is a bacterium, as are the predominant contaminants.

Concentrations of many antibiotics that are safe to use with yeast were inhibitory to growth of *Zymomonas mobilis* strain ZM4, including tetracycline, kanamycin, polymixin and streptomycin (Agrawan and Basappa, Biotechnology Letters (1996) 18:673-678). Only penicillin G was shown to be safe for use with *Zymomonas*. Benzyl penicillin was successfully used to control bacterial contamination in batch *Zymomonas mobilis* fermentation for ethanol production (Grote and Rogers, Journal of Fermentation Technology (1985) 63:287-290). In another review *Zymomonas* was reported as a contaminant of cider and beer, and strains of *Zymomonas* with resistance to typically used levels of some antibiotics including kanamycin, polymyxin, and sreptomycin were found (Swings and De Ley, Bacteriological Reviews (1977) 41:1-46). Differences among strains may be related to the encoding of resistance on plasmids, as was found for streptomycin, kanamycin, and gentamicin in *Z. mobilis* strain CP4 (Walia et al. (1984) Applied and Environmental Microbiology 47:198-200).

There remains a need for methods to control bacterial contaminants in fermentations that use a bacterial *Zymomonas* biocatalyst that has been developed for ethanol production.

SUMMARY OF THE INVENTION

The invention provides fermentation broth compositions and processes for controlling bacterial contamination in media where *Zymomonas* is the biocatalyst.

Accordingly, the invention provides a fermentation broth composition comprising:
  a) fermentation medium;
  b) hop acids; and
  d) a growing population of *Zymomonas* cells.

In another embodiment, the invention provides a method for controlling bacterial contamination in a fermentation using a *Zymomonas* cell biocatalyst comprising:
  a) providing a fermentation medium;
  b) adding hop acids to the fermentation medium;
  c) adding to the fermentation medium an inoculum of *Zymomonas* cells, thereby producing a fermentation broth; and
  d) maintaining the fermentation broth under conditions suitable for growth of the *Zymomonas* cells.

In yet another embodiment the invention provides method for producing ethanol comprising:
  a) providing a fermentation medium;
  b) adding to the fermentation medium an inoculum of *Zymomonas* cells grown in the presence of hop acids, producing a fermentation broth; and
  c) maintaining the fermentation broth under conditions suitable for growth of the *Zymomonas* cells and production of ethanol by the *Zymomonas* cells;
  wherein no hop acids are added to the fermentation medium separately from the inoculum of (b) and wherein ethanol is produced.

DETAILED DESCRIPTION

Figure 1:
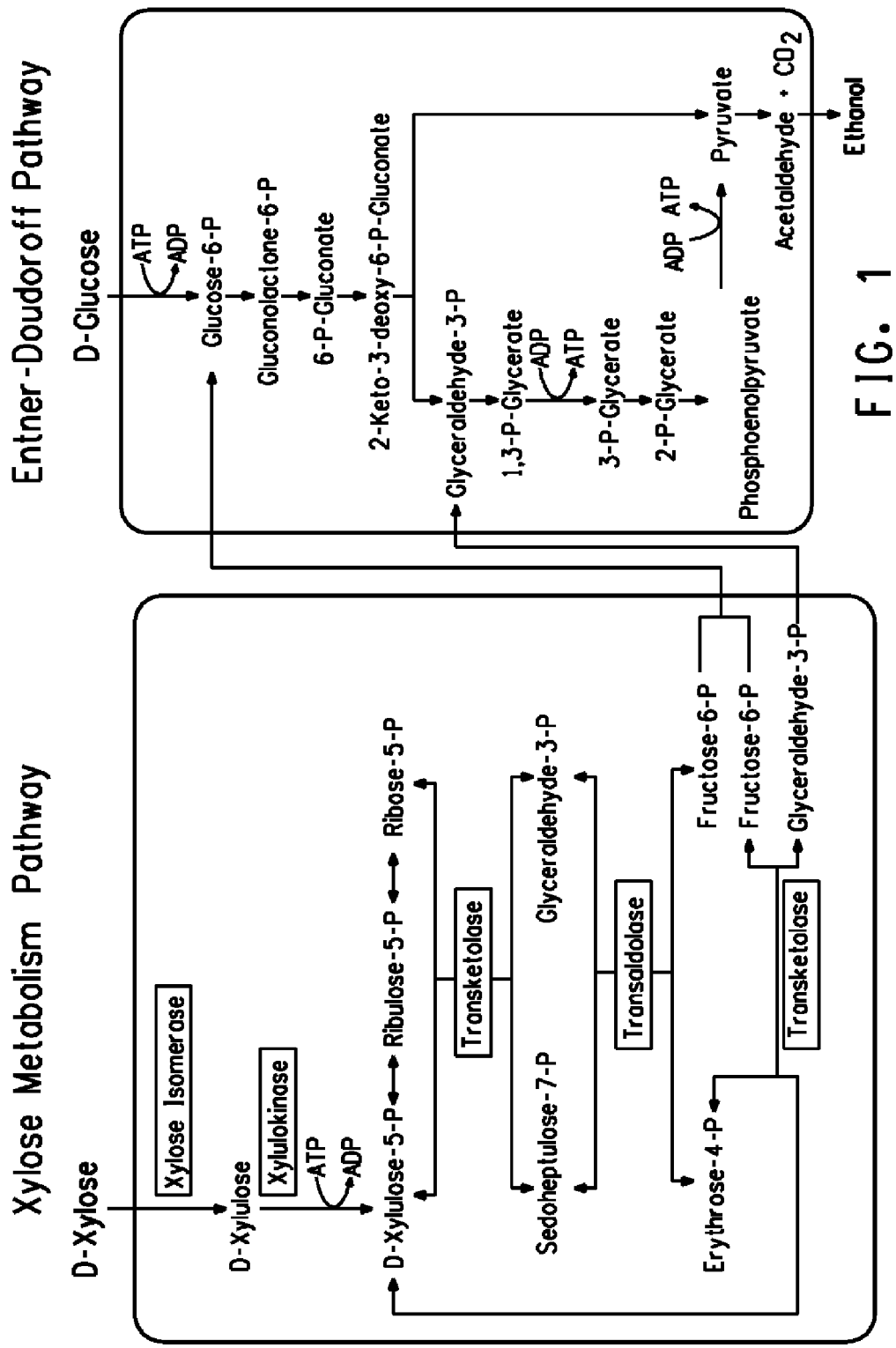
FIG. 1 shows a diagram of the ethanol fermentation pathway in *Zymomonas* engineered for xylose utilization.

The invention relates to the use of an antimicrobial agent to control contaminating bacteria in fermentations that use *Zymomonas* as the biocatalyst, such as for production of ethanol. The finding that hop acids are safe for *Zymomonas* cells while effectively controlling contaminating bacteria allows their use in fermentations where *Zymomonas* is the biocatalyst. In particular, high levels of hop acids, which are higher than levels typically used in fermentations for production of ethanol by yeast, are found to be required for effective control of contaminating bacteria in fermentation media containing cellulosic biomass hydrolysate. The high levels may be used in *Zymomonas* fermentations with no reduction in ethanol production. The efficient production of ethanol from renewable resources, such as cellulosic biomass hydrolysate, for use as a fuel additive will address shortages in fossil fuels, reduce energy costs and impact global warming.

The following definitions and abbreviations are to be use for the interpretation of the claims and the specification.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The term "invention" or "present invention" as used herein is a non-limiting term and is not intended to refer to any single embodiment of the particular invention but encompasses all possible embodiments as described in the specification and the claims.

As used herein, the term "about" modifying the quantity of an ingredient or reactant of the invention employed refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term "about" also encompasses amounts that differ due to different equilibrium conditions for a composition resulting from a particular initial mixture. Whether or not modified by the term "about", the claims include equivalents to the quantities. In one embodiment, the term "about" means within 10% of the reported numerical value, preferably within 5% of the reported numerical value.

The term "ethanologen" refers to an organism that produces ethanol through metabolism of carbohydrate sources.

The term "fermentable sugar(s)" refers to oligosaccharides and monosaccharides that can be used as a carbon source by a microorganism in a fermentation process.

The term "simultaneous saccharification and fermentation (SSF)" refers to a process wherein biomass is saccharified and the fermentable sugars produced from saccharification are used by a biocatalyst to produce a product all at the same time, typically in the same reaction vessel.

The term "cellulosic" refers to a composition comprising cellulose and additional components that may include hemicellulose and lignin.

The term "lignocellulosic" refers to a composition comprising both lignin and cellulose. Lignocellulosic material may also comprise hemicellulose.

The term "saccharification" refers to the production of fermentable sugars from polysaccharides.

The term "biomaterial" refers to any biologically derived material that is a source of carbohydrates that may be used in fermentation by a biocatalyst. Biomaterial includes cellulosic biomass as well as other plant materials and plant-derived materials used as carbohydrate sources such as grains, mash, molasses, and raw juice (such as from sugar beets and sugar cane).

The term "pretreated biomass" means biomass that has been subjected to pretreatment prior to saccharification.

The term "cellulosic biomass" refers to any cellulosic or lignocellulosic material and includes materials comprising cellulose, and optionally further comprising hemicellulose, lignin, starch, oligosaccharides and/or monosaccharides. Cellulosic biomass may also comprise additional components, such as protein and/or lipid. Cellulosic biomass may be derived from a single source, or can comprise a mixture derived from more than one source; for example, cellulosic biomass could comprise a mixture of corn cobs and corn stover, or a mixture of grass and leaves. Cellulosic biomass includes, but is not limited to, bioenergy crops, agricultural residues, municipal solid waste, industrial solid waste, sludge from paper manufacture, yard waste, wood and forestry waste. Examples of cellulosic biomass include, but are not limited to, corn cobs, crop residues such as corn husks, corn stover, grasses, wheat, wheat straw, barley straw, hay, rice straw, switchgrass, palm frond, palm empty fruit bunch, waste paper, sugar cane bagasse, sorghum or soy cellulosic plant material, cellulosic components obtained from milling of grains, trees, branches, roots, leaves, wood chips, sawdust, shrubs and bushes, vegetables, fruits, flowers and animal manure.

The term "cellulosic biomass hydrolysate" refers to the product resulting from saccharification of cellulosic or lignocellulosic biomass. The biomass may also be pretreated prior to saccharification. Cellulosic biomass hydrolysate is a product containing biomass solids.

The term "clarified cellulosic biomass hydrolysate" or "clear cellulosic biomass hydrolysate" refers to a cellulosic biomass hydrolysate which has been processed to remove solids and is not considered to be a cellulosic biomass hydrolysate. In addition, any preparation containing sugars derived from cellulosic biomass.

The term "saccharification enzyme" refers to an enzyme that can catalyze conversion of a component of biomass to fermentable sugars. Typically the enzyme is more effective when the biomass is pretreated.

The term "substantial contamination" refers to a level of lactic acid bacteria contamination in a fermentation broth that would produce more than about 5 g/L of lactic acid if the fermentation broth were incubated without an antimicrobial for about 40 hours.

The term "lactic acid bacteria" refers to bacteria that produce lactic acid as a major metabolic end-product of carbohydrate fermentation. The lactic acid bacteria (LAB) are gram positive bacteria belonging to the order Lactobacillales, and include for example the genera *Lactobacillus, Leuconostoc, Lactococcus, Pediococcus, Streptococcus*, and *Enterococcus*.

The term "fermentation medium" refers to a composition comprising components, such as nutrients, that support the growth of a microorganism used as a biocatalyst. Fermentation medium may be used in any size including small scale cultures and large scale production fermentations.

The term "fermentation broth" refers to a composition comprising fermentation medium and biocatalyst cells in which fermentation is occurring or has occurred. Depending on how long the biocatalyst has been grown in the fermentation broth, this broth may also include the product produced by the biocatalyst, such as ethanol.

The term "seed culture" is a culture of biocatalyst cells that is used to inoculate a larger volume of fermentation medium producing a fermentation broth. Typically a seed culture inoculum is about 0.01% to 20% v/v of the final volume of the fermentation broth.

The term "contamination" refers to the presence of microorganisms that are not intentionally introduced. Typically a desired biocatalyst is introduced into a growth medium producing a fermentation broth. Microorganisms present in the fermentation broth other than the introduced biocatalyst are considered to be contamination.

The term "hop acids" refers to a product obtained from hops, which are female flower clusters (commonly called seed cones or strobiles) of the hops plant *Humulus lupulu*, by carbon dioxide ($CO_2$) extraction. The $CO_2$ extracted hop acids are composed of alpha acids (also called humulone) and beta acids, both of which are considered to be hop acids. The hop alpha acids fraction of the $CO_2$ extract is typically separated from the remainder of the hop extract. Isomerized hop alpha acids (iso-alpha acids) are produced by boiling and are also considered to be hop acids. Derivatives of hop iso-alpha acids are also made by chemical reductions, producing rho-iso-alpha acids, tetrahydroiso-alpha-acids, and hexahydroiso-alpha-acids, which are also considered to be hop acids. Hop beta acids include, but are not limited to, colupulone, lupulone, and adlupulone. Hop acids are commonly used in the brewing of beer where hop alpha acids contribute bitter flavor in beer, and also have a mild antibiotic/bacteriostatic effect against gram positive bacteria while not affecting the activity of brewing yeast. Hop beta acids contribute to bitter aroma of beer.

The present compositions and methods provide for control of undesired bacteria in cultures where a *Zymomonas* bacterium is the biocatalyst, such as in fermentation for ethanol production. Undesired, contaminating bacteria are typically present in large scale processes, particularly when media contain processed biomaterial. Processed biomaterial used in media may include carbohydrate sources such as corn or wheat mash, sugar beet or sugar cane molasses, and cellulosic or lignocellulosic biomass hydrolysate. Contaminating bacteria may be introduced in a fermentation process from biomaterial, process equipment, inoculation cultures, process water, air, or other sources. Controlling contamination in a production fermentation typically allows the biocatalyst to grow and produce product to a higher level than that achieved in the presence of contaminating bacteria, providing a more efficient and economical fermentation process.

Antimicrobial Agent for *Zymomonas* Fermentations

Since *Zymomonas* itself is a bacterium, for an antimicrobial agent to be used in *Zymomonas* fermentations it must selectively target the contaminating bacteria while not affecting the *Zymomonas* bacteria. The predominant contaminating bacteria in large-scale fermentations using biomaterial-derived carbohydrate sources are lactic acid bacteria (LAB), such as strains of *Lactobacillus*. LAB are gram positive while *Zymomonas* is gram negative. The challenge was thus to identify an antimicrobial agent that controls LAB in fermentation media, without negative impact on growth and ethanol production of *Zymomonas* cells. Other contaminating bacteria in addition to LAB may be controlled by this type of antimicrobial agent.

The present method uses hop acids as a selective antimicrobial agent for use in *Zymomonas* fermentations. It is found herein that hop acids are safe for use to control contamination in *Zymomonas* cultures. Hop acids are obtained from the female flower clusters of the hops plant *Humulus lupulu*, by carbon dioxide ($CO_2$) extraction. The extracted material may be further separated and/or chemically modified to produce different types of hop acids. Various types of hop acids preparations are commercially available such as LactoStab®, IsoStab®, BetaStab®, and LupuStab® from BetaTec, Hop Products Inc. (John I. Haas, Inc., Washington, D.C.), and Beta Bio 45%, Hopsteiner® Iso-Extract-30%, Tetra Iso-Extract, and Hexa Iso-Extract from Hopsteiner®, S.S. Steiner, Inc. (New York, N.Y.).

The actual amount of hop acids in each commercial product can be determined using the manufacturer's technical specifications which provide the percent and type of hop acids in the product preparation as follows. LactoStab® is a preparation that is 8.5%-9.5% hop bitter acids. IsoStab® is a preparation that is 29.5%-30.5% iso-alpha acids. Beta Bio 45% is a preparation that is 45% natural hop beta-acids, including colupulone, lupulone, and adlupulone. Iso-Extract-30% is a preparation of hop alpha-acids that are isomerized by boiling, with a concentration of 30.0+/−1.0% (W/W) of iso-alpha-acids. Tetra Iso-Extract (tetrahydroiso-alpha-acids) and Hexa Iso-Extract hexahydroiso-alpha-acids are preparations of derivatives of hop iso alpha-acids made by chemical reductions containing 9.0% tetrahydroiso-alpha-acids or hexahydroiso-alpha-acids, respectively. Hexa Iso-Extract also contains 1.0% of tetrahydroiso-alpha-acids. Any of these or other preparations of hop acids may be used in the present compositions and methods.

Preparations of hop acids are recommended for use in ethanol fermentations that use yeast as a biocatalyst at the following doses: Beta Bio 45% added to molasses based feed stocks at 5 ppm, with 5-10 ppm (equivalent to 2.75-4.5 ppm of hop beta-acids) as an effective dose; Iso-Extract-30% added to yeast propagators, mash tanks, and fermenters of cereal based fermentation plants at 50 ppm (equivalent to 15 ppm of hop alpha-acids). Tetra Iso-Extract and Hexa-Iso Extract have been shown to inhibit growth of gram positive bacteria at 40 ppm (about 3.6 ppm of hop acids).

In one aspect, in the present method hop acids and an inoculum of *Zymomonas* cells are added to a fermentation medium producing a fermentation broth, which is maintained under conditions suitable for growth of the *Zymomonas* cells. The hop acids and inoculum may be added to the medium in either order, or concurrently. The present fermentation broth compositions comprise fermentation medium, hop acids, and a growing population of *Zymomonas* cells as described below. Once the fermentation medium is inoculated with *Zymomonas* cells such as cells from a freezer stock, cells revived from a freezer stock, or cells in a seed culture, the *Zymomonas* cells grow forming a growing population of *Zymomonas* cells.

The fermentation medium may be of any type that supports growth and production by *Zymomonas* cells. One skilled in the art will know how to prepare any of the described types of media in view of the information below. In one embodiment the fermentation medium is a defined medium. This medium contains typical purchased components including a carbohydrate source such as glucose, a source of amino acids and other nutrients such as yeast extract, and other components that may include trace elements, nitrogen, and phosphorus such as $KH_2PO_4$ and $MgSO_4$. Defined medium is often used for growing laboratory scale cultures as well as seed cultures that are used as inoculum for large scale fermentations.

In another embodiment the fermentation medium contains sugars obtained from non-cellulosic materials such as mash, raw juice, or molasses. These sugars are prepared from biomaterials such as cereal grains (such as corn, wheat, barley and rye) and sugar crops such as sugar beets and sugar cane. Hydrolyzed mash used for fermentation is made from cereal grains typically by heating to a temperature above the gelatinization temperature, treating with alpha amylase to liquefy, and saccharifying using enzymes such as glucoamylase. Molasses or raw juice from sugar beets and sugar cane may be used as the sugar source in fermentation medium. This type of sugar source is a non-cellulosic biomaterial sugar source (cellulosic includes lignocellulosic), since the sugar source is primarily starch or sugar juice. This type of sugar source is typically used in seed cultures and in the production of ethanol using yeast as a biocatalyst, and in other non-cellulosic large scale fermentations.

Defined media and media having sugar from a non-cellulosic source lack cellulosic (including lignocellulosic) biomass hydrolysate. Additionally, media containing a sugar source that is obtained from cellulosic biomass, and is highly purified to remove other cellulosic components such as solids, is considered to be medium lacking cellulosic biomass hydrolysate. This type of medium contains a clarified cellulosic biomass hydrolysate.

In yet another embodiment the fermentation medium contains cellulosic biomass hydrolysate prepared from cellulosic (including lignocellulosic) biomaterials. Cellulosic biomass hydrolysate contains biomass solids. Cellulosic biomass hydrolysate is produced by saccharification of cellulosic (including lignocellulosic) biomass. Typically the biomass is pretreated prior to saccharification. Biomass may be treated by any method known by one skilled in the art to produce fermentable sugars in a hydrolysate. Typically the biomass is pretreated using physical and/or chemical treatments, and saccharified enzymatically. Physical and chemical treatments may include grinding, milling, cutting, base treatment such as with ammonia or NaOH, and/or acid treatment. Particularly useful is a low ammonia pretreatment where biomass is contacted with an aqueous solution comprising ammonia to form a biomass-aqueous ammonia mixture where the ammonia concentration is sufficient to maintain an alkaline pH of the biomass-aqueous ammonia mixture but is less than about 12 wt. % relative to dry weight of biomass, and where dry weight of biomass is at least about 15 wt % solids relative to the weight of the biomass-aqueous ammonia mixture, as disclosed in commonly owned U.S. Pat. No. 7,932,063, which is herein incorporated by reference.

Enzymatic saccharification typically makes use of an enzyme composition or blend to break down cellulose and/or hemicellulose and to produce a hydrolysate containing sugars such as, for example, glucose, xylose, and arabinose. Saccharification enzymes are reviewed in Lynd, L. R., et al. (Microbiol. Mol. Biol. Rev., 66:506-577, 2002). At least one enzyme is used, and typically a saccharification enzyme blend is used that includes one or more glycosidases. Glycosidases hydrolyze the ether linkages of di-, oligo-, and polysaccharides and are found in the enzyme classification EC 3.2.1.x (Enzyme Nomenclature 1992, Academic Press, San Diego, Calif. with Supplement 1 (1993), Supplement 2 (1994), Supplement 3 (1995, Supplement 4 (1997) and Supplement 5 [in Eur. J. Biochem., 223:1-5, 1994; Eur. J. Biochem., 232:1-6, 1995; Eur. J. Biochem., 237:1-5, 1996; Eur. J. Biochem., 250:1-6, 1997; and Eur. J. Biochem., 264:610-650 1999, respectively]) of the general group "hydrolases" (EC 3.). Glycosidases useful in the present method can be categorized by the biomass components they hydrolyze. Glycosidases useful for the present method include cellulose-hydrolyzing glycosidases (for example, cellulases, endoglucanases, exoglucanases, cellobiohydrolases, β-glucosidases), hemicellulose-hydrolyzing glycosidases (for example, xylanases, endoxylanases, exoxylanases, β-xylosidases, arabino-xylanases, mannases, galactases, pectinases, glucuronidases), and starch-hydrolyzing glycosidases (for example, amylases, α-amylases, β-amylases, glucoamylases, α-glucosidases, isoamylases). In addition, it may be useful to add other activities to the saccharification enzyme consortium such as peptidases (EC 3.4.x.y), lipases (EC 3.1.1.x and 3.1.4.x), ligninases (EC 1.11.1.x), or feruloyl esterases (EC 3.1.1.73) to promote the release of polysaccharides from other components of the biomass. It is known in the art that microorganisms that produce polysaccharide-hydrolyzing enzymes often exhibit an activity, such as a capacity to degrade cellulose, which is catalyzed by several enzymes or a group of enzymes having different substrate specificities. Thus, a "cellulase" from a microorganism may comprise a group of enzymes, one or more or all of which may contribute to the cellulose-degrading activity. Commercial or non-commercial enzyme preparations, such as cellulase, may comprise numerous enzymes depending on the purification scheme utilized to obtain the enzyme. Many glycosyl hydrolase enzymes and compositions thereof that are useful for saccharification are disclosed in WO 2011/038019.

Saccharification enzymes may be obtained commercially. Such enzymes include, for example, Spezyme® CP cellulase, Multifect® xylanase, Accelerase® 1500, and Accellerase® DUET (Danisco U.S. Inc., Genencor International, Rochester, N.Y.), and Novosyme-188 (Novozymes, 2880 Bagsvaerd, Denmark). In addition, saccharification enzymes may be unpurified and provided as a cell extract or a whole cell preparation. The enzymes may be produced using recombinant microorganisms that have been engineered to express one or more saccharifying enzymes. For example, the H3A protein preparation used herein for saccharification of pretreated cellulosic biomass is an unpurified preparation of enzymes produced by a genetically engineered strain of *Trichoderma reesei*, which includes a combination of cellulases and hemicellulases and is described in WO 2011/038019, which is incorporated herein by reference.

Additional enzymes for saccharification include, for example, glycosyl hydrolases such as members of families GH3, GH39, GH43, GH55, GH10, and GH11. GHs are a group of enzymes that hydrolyze the glycosidic bond between two or more carbohydrates, or between a carbohydrate and a noncarbohydrate moiety. Families of GHs have been classified based on sequence similarity and the classification is available in the Carbohydrate-Active enzyme (CAZy) database (Cantarel et al. (2009) Nucleic Acids Res. 37 (Database issue):D233-238). Certain of these enzymes are able to act on various substrates and have demonstrated effecacy as saccharification enzymes. Glycoside hydrolase family 3 ("GH3") enzymes have a number of known activities, including, for example, β-glucosidase (EC:3.2.1.21); β-xylosidase (EC:3.2.1.37); N-acetyl β-glucosaminidase (EC: 3.2.1.52); glucan β-1,3-glucosidase (EC:3.2.1.58); cellodextrinase (EC:3.2.1.74); exo-1,3-1,4-glucanase (EC:3.2.1); and/or β-galactosidase (EC 3.2.1.23) activities. Glycoside hydrolase family 39 ("GH39") enzymes also have a number of known activities, including, for example, α-L-iduronidase (EC:3.2.1.76) and/or β-xylosidase (EC:3.2.1.37) activities. Glycoside hydrolase family 43 ("GH43") enzymes have a number of known activities including, for example, L-α-arabinofuranosidase (EC 3.2.1.55); β-xylosidase (EC 3.2.1.37); endoarabinanase (EC 3.2.1.99); and/or galactan 1,3-β-galactosidase (EC 3.2.1.145) activities. Glycoside hydrolase family 51 ("GH51") enzymes are known to have, for example, L-α-arabinofuranosidase (EC 3.2.1.55) and/or endoglucanase (EC 3.2.1.4) activities. Glycoside hydrolase family 10 ("GH10") have beendescribed in detail in Schmidt et al., 1999, Biochemistry 38:2403-2412 and Lo Leggio et al., 2001, FEBS Lett 509: 303-308) and the Glycoside hydrolase family 11 ("GH11") have been described in Hakouvainen et al., 1996, Biochemistry 35:9617-24.

Fermentation media containing biomass hydrolysate may contain a percent of hydrolysate with one or more additional sugars and/or other added components, or the media may contain 90% or more hydrolysate with minor additions such as sorbitol, as described below. In various embodiments cellulosic biomass hydrolysate is at least about 50%, 60%, 70%, 80%, 90% or 95% of the final volume of fermentation broth. Typically about 10% of the final volume of fermentation broth is seed inoculum.

The solids content of biomass hydrolysate is typically between about 10% and 40%, depending on the pretreatment and saccharification methods employed. More typically the solids content is about 25%, with a medium containing 90% cellulosic biomass hydrolysate having about 23% solids.

Hop Acids Concentration in Fermentation Broths

The concentration of hop acids that is needed to control contamination in a *Zymomonas* fermentation broth was found herein to vary, depending on whether the fermentation medium contains cellulosic biomass hydrolysate. It is found herein that in media lacking cellulosic biomass hydrolysate, (described above) a concentration of about 7.5 ppm hop acids was effective to control contaminating bacteria without affecting the *Zymomonas* cells. Hop acids may be used in the present methods and compositions with medium lacking cellulosic biomass hydrolysate in a concentration of at least about 2, 5, 7.5, 10, 15, 20, 25, 30, 35, 40, 45, 50 ppm or more including any integer or fraction therebetween. The amount of hop acids needed to control contamination depends on factors such as the amount of contamination, type of medium, specific preparation of hop acids, concentration of *Zymomonas* cells following inoculation, and the fermentation conditions, and can be determined by one skilled in the art for a specific situation.

Control of contaminating bacteria may be assessed by determining the level of lactic acid in the fermentation broth, where the presence of less than about 5 g/L of lactic acid after about 40 hours of fermentation indicates that contamination is controlled. Contamination may be controlled at less than about 5 g/L of lactic acid in the fermentation broth, or less than 4 g/L or 3 g/L or 2 g/L or 1 g/L of lactic acid. The amount of lactic acid in fermentation broth is typically assayed by HPLC, as is known by one skilled in the art.

It is found herein that when contamination present in a seed culture is controlled by using hop acids (as described above), and the seed culture is used to inoculate a larger scale fermentation, contamination remains controlled in the large scale fermentation without adding hop acids or other anti-microbial agent to the fermentation medium separately from the inoculum. Thus in one embodiment, contamination is controlled in a fermentation by the inclusion of hop acids in a seed culture that is used to inoculate the fermentation medium. The fermentation medium may contain cellulosic biomass hydrolysate, or lack cellulosic biomass hydrolysate. In a seed culture grown in medium lacking cellulosic biomass hydrolysate, the concentration of hop acids may be as described above: at least about 2, 5, 7.5, 10, 15, 20, 25, 30, 35, 40, 45, 50 ppm or more including any integer or fraction therebetween. Typical embodiments use hop acids at a concentration that is between about 2 ppm and 20 ppm. More typical embodiments use hop acids at concentrations that are between about 3 ppm and about 10 ppm.

However when contamination is not controlled in a seed culture, contamination is a factor in a large scale fermentation that is inoculated with the contaminated seed culture. In one embodiment contamination in the contaminated seed-inoculated fermentation is controlled as described above when using medium lacking cellulosic biomass hydrolysate.

It is found herein that in fermentation broth containing media containing cellulosic biomass hydrolysate, a concentration of greater than about 30 ppm of hop acids is needed to control contaminating bacteria. In experiments herein, concentrations of 150 ppm and 750 ppm were able to keep the lactic acid production level below 5 g/L when a contaminated seed culture was used to inoculate a hydrolysate medium. In fermentation broth containing media containing cellulosic biomass hydrolysate, a concentration of hop acids of greater than about 30, 40, 50, 60, 70, 80, 90, 100, 150, 200, 250, 300, 350, 400, 450, 500, 550, 600, 650, 700, 750 ppm or more including any integer or fraction therebetween is used to control contamination in a *Zymomonas* cell fermentation.

The presence of relatively high solids in cellulosic biomass hydrolysate containing medium, and the effect that the solids have on mixing, may contribute to the requirement for the higher levels of hop acids needed to control contamination as compared to levels that are effective in medium lacking cellulosic biomass hydrolysate. The presence of various biomass degradation products in hydrolysate may also contribute. The high levels of hop acids are greater than those recommended for use in yeast ethanol production by the manufacturers of hop acids products.

In any type of medium used for fermentation, specific amounts of hop acids needed to achieve effective contamination control results will depend on factors including growth and production characteristics of the *Zymomonas* strain used, the contaminating microorganisms present, the initial contamination level, specific preparation of hop acids, the type and amount of cellulosic biomass hydrolysate in the medium (includes percent solids and toxicity of hydrolysate by-products to contaminating and *Zymomonas* cells) if present, and culture conditions including mixing. One of skill in the art can readily determine the concentration of hop acids relative to the amounts disclosed herein that is effective in controlling contamination in a specific *Zymomonas* fermentation broth while maintaining maximal *Zymomonas* cell productivity.

Inoculum of *Zymomonas* Cells

In the present method the inoculum of *Zymomonas* cells may be any source of *Zymomonas* cells that is effective in starting a growing culture. Typically, *Zymomonas* cells are stored as frozen stocks, and cells are revived by growing in a small culture in defined medium. The small culture is used as an inoculum that is added to fermentation medium to produce a fermentation broth, or culture. A small culture may also be used to inoculate a seed culture. The *Zymomonas* cells are grown in the seed culture, which is then added as an inoculum to a larger scale fermentation. A seed culture used as an inoculum may contain sterile defined medium with no hop acids needed to control contamination. Alternatively, a seed culture used as an inoculum may contain defined medium or other medium lacking cellulosic biomass hydrolysate, such as medium prepared from mash or molasses, that may be contaminated such as by process equipment, where hop acids are added to control contamination as described above. In addition, a seed culture used as an inoculum may contain cellulosic biomass hydrolysate and hop acids to control contamination as described above.

*Zymomonas* Cells

Any strain of *Zymomonas* cells may be used in the present compositions and methods, and is selected based on factors including the type of medium to be used and the desired output of the fermentation process. Any strain of *Zymomonas* that is an effective biocatalyst for the desired production process may be used. For example, *Zymomonas* cells naturally produce ethanol using glucose, fructose and/or sucrose as fermentation substrates, but xylose is not metabolized. In one embodiment the *Zymomonas* cells used in the present methods and compositions have been engineered for xylose utilization, which is particularly desired when using cellulosic biomass hydrolysate, which contains xylose.

Strains of ethanol-producing *Zymomonas*, such as *Z. mobilis* have been engineered for xylose fermentation to ethanol. Typically four genes have been introduced into *Z. mobilis* for expression of four enzymes involved in xylose metabolism to create a xylose utilization metabolic pathway (FIG. 1) as described in U.S. Pat. No. 5,514,583, U.S. Pat. No. 5,712,133, U.S. Pat. No. 6,566,107, WO 95/28476, Feldmann et al. ((1992) Appl Microbiol Biotechnol 38: 354-361), and Zhang et al. ((1995) Science 267:240-243). These include genes encoding xylose isomerase which catalyzes the conversion of xylose to xylulose, and xylulokinase which phosphorylates xylulose to form xylulose 5-phosphate. Additionally expressed are transketolase and transaldolase, two enzymes of the pentose phosphate pathway that convert xylulose 5-phosphate to intermediates that couple pentose metabolism to the glycolytic Entner-Douderoff pathway permitting the metabolism of xylose to ethanol (see FIG. 1). DNA sequences encoding these enzymes may be obtained from any of numerous microorganisms that are able to metabolize xylose, such as enteric bacteria, and some yeasts and fungi. Sources for the coding regions may include *Xanthomonas, Klebsiella, Escherichia, Rhodobacter, Flavobacterium, Acetobacter, Gluconobacter, Rhizobium, Agrobacterium, Salmonella, Pseudomonads*, and *Zymomonas*. The coding regions of *E. coli* are typically used.

The encoding DNA sequences are operably linked to promoters that are expressed in *Zymomonas* cells such as the promoter of *Z. mobilis* glyceraldehyde-3-phosphate dehydrogenase (GAP promoter), and *Z. mobilis* enolase (ENO promoter). A mutant GAP promoter with increased expression as disclosed in U.S. Pat. No. 7,989,206, which is incorporated herein by reference, is also useful for expression in *Zymomonas*. The coding regions may individually be expressed from promoters, or two or more coding regions may be joined in an operon with expression from the same promoter. The resulting chimeric genes may be introduced into *Zymomonas* cells and maintained on a plasmid, or integrated into the genome using, for example, homologous recombination, site-directed integration, or random integration. Examples of strains engineered to express a xylose utilization metabolic pathway include CP4(pZB5) (U.S. Pat. No. 5,514,583), ATCC31821/pZB5 (U.S. Pat. No. 6,566,107), 8b (US 20030162271; Mohagheghi et al., (2004) Biotechnol. Lett. 25; 321-325), and ZW658 (ATTCC # PTA-7858). Cells of *Zymomonas* that are engineered for expression of the xylose utilization metabolic pathway generally require a period of adaptation in xylose-containing medium prior to being able to grow in medium that contains xylose as the only sugar.

In additional embodiments the *Zymomonas* cells have one or more additional genetic modification that improves the strain such as one that increases growth rate and/or cell mass, increases utilization of xylose and/or allows use of other sugars such as arabinose, increases tolerance to inhibitory compounds such as acetate, or increases production of ethanol.

In one embodiment *Zymomonas* cells may be additionally engineered for arabinose utilization which is described in U.S. Pat. No. 5,843,760, which is incorporated herein by reference. To allow arabinose utilization, genes expressed in addition to genes of the xylose utilization pathway include: 1) L-arabinose isomerase to convert L-arabinose to L-ribulose, 2) L-ribulokinase to convert L-ribulose to L-ribulose-5-phosphate, and 3) L-ribulose-5-phosphate-4-epimerase to convert L-ribulose-5-phosphate to D-xylulose (U.S. Pat. No. 5,843,760). As disclosed in US 2011/0143408, which is incorporated herein by reference, improved arabinose utilization may be achieved by additionally expressing an arabinose-proton symporter, such as by expressing a coding region from an araE gene.

In another embodiment the endogenous himA gene, which encodes the alpha subunit of the integration host factor, is genetically modified to reduce its expression which improves growth in medium containing acetate as described in U.S. Pat. No. 7,897,396, which is incorporated herein by reference. Acetate is present in biomass hydrolysate, thus when using medium containing biomass hydrolysate, increased tolerance to this component is desired.

In another embodiment a genetic modification is made that reduces glucose-fructose oxidoreductase (GFOR) activity as described in U.S. Pat. No. 7,741,119, which is incorporated herein by reference. Reduced expression of GFOR, as well as of the himA gene, may be by any method such as those described above for reducing aldose reductase activity.

In another embodiment a genetic modification is made which increases ribose-5-phosphate isomerase (RPI) activity, as disclosed in commonly owned and co-pending U.S. patent application Ser. No. 13/161,734, which is incorporated herein by reference. Increased RPI expression may be accomplished by increasing expression of the endogenous RPI encoding gene, such as with a promoter that is more highly active than the native promoter, or by expressing a heterologous gene encoding any protein or polypeptide with ribose-5-phosphate isomerase activity in *Zymomonas*. There are two groups of ribose-5-phosphate isomerase enzymes that are called RPI-A and RPI-B, as described in U.S. application Ser. No. 13/161, 734, either of which may be expressed.

In another embodiment, the xylose isomerase that is expressed as part of the xylose utilization metabolic pathway is expressed using a mutant, highly active promoter that is disclosed in U.S. Pat. No. 7,989,206 and U.S. Pat. No. 7,998, 722, which are incorporated herein by reference. The mutant promoters disclosed therein are promoters of the *Zymomonas mobilis* glyceraldehyde-3-phosphate dehydrogenase gene.

In another embodiment a xylose isomerase that is expressed as part of the xylose utilization metabolic pathway is a Group I xylose isomerase included in the class of enzymes identified by EC 5.3.1.5 as disclosed in commonly owned and co-pending US Patent Publication US 2011-0318801. It is disclosed therein that Group I xylose isomerases, such as one expressed from a coding region isolated from *Actinoplanes missouriensis* have higher activity in *Zymomonas* than Group 2 xylose isomerase. Group I xylose isomerases are defined therein by molecular phylogenetic bioinformatics analysis (using PHYLIP neighbor joining algorithm as implemented in PHYLIP (Phylogeny Inference Package version 3.5c; Felsenstein (1989) Cladistics 5:164-166), GroupSim analysis (Capra and Singh (2008) Bioinformatics 24: 1473-1480), and a Profile Hidden Markov Model (using the hmmsearch algorithm of the HMMER software package; Janelia Farm Research Campus, Ashburn, Va.).

In another embodiment the *Zymomonas* cells have been adapted for growth in a stress culture containing ethanol and ammonium acetate as disclosed in US Patent Application Publication 2011-0014670-A1, which is incorporated herein by reference. These *Zymomonas* strains with improved acetate tolerance are particularly useful when using cellulosic biomass hydrolysate containing fermentation medium, which contains acetate.

Strains disclosed in the above references provide examples of strains that may be used in the present methods and include ATCC31821/pZB5, ZW658 (ATCC #PTA-7858), ZW800, ZW801-4, ZW801-4::ΔhimA, AcR#3, and ZW705.

*Zymomonas* Fermentation

In the present method the inoculated culture medium, or fermentation broth, is incubated under conditions suitable for growth of *Zymomonas* cells. In one embodiment the *Zymomonas* cells are of a strain of *Zymomonas* that is an effective biocatalyst for the production of ethanol under conditions used in fermentation, and ethanol is produced in the fermentation broth. When the sugars concentration in the fermentation medium is high such that growth is inhibited, the medium includes sorbitol, mannitol, or a mixture thereof as disclosed in commonly owned U.S. Pat. No. 7,629,156, which is incorporated herein by reference. Typically a final concentration of about 5 mM sorbitol or mannitol is present in the medium.

Typically conditions are used with temperature that is between about 30° C. and about 37° C., and with pH of about 4.5 to about 7.5. Typically cultures are incubated without supplemented air, oxygen, or other gases (which may include conditions such as anaerobic, microaerobic, or microaerophilic fermentation), for at least about 20 hours, and may be run for about 25, 30, 35, 40, 45, 50, 55, 60, 65, 70 hours or longer. Typically seed cultures are incubated for about 20 hours, while fermentation production cultures are incubated for about 40 hours or more. In order to minimize foaming, antifoam agents (any class-silicone based, organic based etc) may be added to the medium as needed.

For commercial production fermentation cultures, a variety of culture methodologies may be applied. For example, large-scale production may use both batch and continuous culture methodologies. A classical batch culturing method is a closed system where the composition of the medium is set at the beginning of the culture and not subjected to artificial alterations during the culturing process. Thus, at the beginning of the culturing process the medium is inoculated with the desired organism and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of ethanol.

A variation on the standard batch system is the Fed-Batch system. Fed-Batch culture processes are also suitable for the present methods and compositions, and comprise a typical batch system with the exception that the substrate is added in increments as the culture progresses. Measurement of the actual substrate concentration in Fed-Batch systems is difficult and is therefore estimated on the basis of the changes of measurable factors such as pH and the partial pressure of waste gases such as $CO_2$. Batch and Fed-Batch culturing methods are common and well known in the art and examples may be found in Biotechnology: A Textbook of Industrial Microbiology, Crueger, Crueger, and Brock, Second Edition (1989) Sinauer Associates, Inc., Sunderland, M A, or Deshpande, Mukund V., *Appl. Biochem. Biotechnol.*, 36, 227, (1992)

The present methods and compositions may also be used in a continuous culture process. Continuous cultures are open systems where culture medium is added continuously to a bioreactor and an equal amount of conditioned medium is removed simultaneously for processing. Continuous cultures generally maintain the cells at a constant high liquid phase density where cells are primarily in log phase growth. Alternatively, continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials as is known to one skilled in the art.

In a production process, production fermentation cultures are typically run one after the other until a clean-out of the system is necessary.

The present methods and compositions may also be used in a simultaneous saccharification and fermentation (SSF) process. For example, the process disclosed in US Patent Application Publication 2011-0318803, which is incorporated herein by reference, may be used. In this SSF process *Zymomonas* cells are grown under conditions of low impeller agitation with high concentration of insoluble solids in a saccharification-fermentation mixture during a simultaneous saccharification and fermentation reaction for the production of high concentrations of ethanol. In addition, a hybrid saccharification and fermentation (HSF) process may be used in which partial saccharification is carried out prior to addition of Zymomonas cells, then further saccharification and fermentation occur simultaneously.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various uses and conditions.

The meaning of abbreviations is as follows: "hr" means hour(s), "min" means minute(s), "sec" means second(s), "d" means day(s), "L" means liter(s), "mL" means milliliter(s), "μL" means microliter(s), "g" means grams, "μg" means microgram(s), "ng" means nanogram(s), "g/L" means grams per liter, "mM" means millimolar, "μM" means micromolar, "nm" means nanometer(s), "μmol" means micromole(s), "pmol" means picomole(s), "OD600" means optical density measured at 600 nm, "EFT" means elapsed fermentation time, "ppm" means parts per million.

General Methods
Media

MRS medium has 10 g/L peptone, 8 g/L meat extract, 4 g/L yeast extract, 20 g/L glucose, 5 g/L sodium acetate trihydrate, 1 g/L Tween 80, 2 g/L $K_2HPO_4$, 2 g/L triammonium citrate, 0.2 g/L $MgSO_4*7H_2O$, 0.05 g/L $MnSO_4*4H_2O$, pH 6.2

Cob Composition

The amount of cellulose and xylan in starting corn cob was determined using the method ASTM E1758-01 "Standard method for the determination of carbohydrates by HPLC" as further detailed n National Renewable Energy Laboratory (Golden, Colo.) Technical Report NREL/TP-510-42618 (revised April 2008). The composition was determined to be 34.8% cellulose, 29.2% xylan, 12.8% lignin based on dry weight.

Saccharification Enzymes

Spezyme® CP cellulase and Multifect®-CX12L were from Danisco U.S. Inc., Genencor International, Rochester, N.Y.

Novozyme-188 was from Novozymes (2880 Bagsvaerd, Denmark).

H3A Protein

H3A protein was prepared from the genetically engineered H3A strain of Trichoderma reesei. Strain H3A was prepared as described in U.S. Pat. No. 7,666,648. Briefly, a Trichoderma reesei mutant strain, derived from RL-P37 (Sheir-Neiss, G et al. Appl. Microbiol. Biotechnol. 1984, 20:46-53) and selected for high cellulase production was co-transformed with a β-glucosidase expression cassette and an endoxylanase expression cassette using electroporation. One transformant was called strain #229. Strain #229 was co-transformed with a β-xylosidase Fv3A expression cassette, a β-xylosidase Fv43D expression cassette, and a Fv51A α-arabinofuranosidase expression cassette using electroporation. Strain H3A was isolated from this transformation step.

Extracellular proteins produced during fermentation of strain H3A were separated from the cell mass by centrifugation, concentrated by membrane-ultrafiltration through a Millipore 10 kD molecular cut off weight membrane, and pH adjusted to 4.8. Total protein was determined using a modified Biuret method as modified by Weichselbaum and Gornall using Bovine Serum Albumin as a calibrator (Weichselbaum, 1960, Amer. J. Clin. Path. 16:40; Gornall et al., 1949 J. Biol. Chem. 177:752). This H3A extracellular protein preparation, also termed herein as H3A protein, was used as a combination cellulase and hemicellulase preparation effecting complex carbohydrate hydrolysis during SSF.

Cob Hydrolysate Hydrolysate MD07#3
Pretreatment

Batches of corn cob were processed with a hammermill (Glen Mills Inc., Clifton, N.H.), passed through a ⅜ inch (0.95 cm) or a 3/16 inch (0.48 cm) screen and treated with 6%, 8%, or 10% ammonia relative to dry weight biomass in a 170 L Jaygo reactor (Jaygo Manufacturing, Inc., Mahwah, N.J.) held at 145° C. for 20 min. Prior to injecting the aqueous ammonia the reactor was evacuated to ~0.1 bar (10 kilopascal), and after the 20 min period the reactor was flashed in 2 stages to ~0.1 bar (10 kilopascal). The final solids concentration for the pretreated cob mixture was about 60%.

Saccharification

The MD07#3 hydrolysate was generated in a 1000 L fermenter, equipped with a recirculation loop. A water heel (542.3 kg) was added to the fermenter and sterilized at 121° C. for 20 minutes. The water was cooled to 47° C. and the pretreated cob mixture was added through a feeder, situated on the top of the tank; 112.1 kg were added at this time. The pH was adjusted to 5.3 with 9.8 wt % $H_2SO_4$ and a first dose of enzymes was added. See Table 2 for the mass of the enzymes used and the corresponding dosages. Over the following nine hours, an additional 317.6 kg of pretreated corn cobs were added, with the pH controlled to 5.3 with 9.8 wt % $H_2SO_4$ throughout the additions. The target solids loading for this run was 25 wt %. At 12 hours after the first enzyme addition, a second dose was added (see Table 1). The fermenter was controlled at 47° C. and pH 5.3 for approximately 96 hours and the slurry was circulated through the recirculation loop. Starting at three hours after the first enzyme addition, a rotor-stator grinder in the recirculation loop was intermittently used to reduce the particle size of the pretreated cobs in the slurry. The grinder was used nine times for anywhere from 30 to 110 minutes at a time. At the end of the 96-hour run, some hydrolysate material was drawn off for use in these experiments. A sample of the hydrolysate was analyzed and the remainder was stored refrigerated until use. The results of the sample analysis are contained in Table 2.

TABLE 1

Enzymes used in MD07#3 saccharification

| Enzyme Name | Mass First Addition (kg) | Mass Second Addition (kg) | Overall Dosage (mg Protein/g glucan + xylan) |
|---|---|---|---|
| Spezyme ® CP | 3.72 | 14.77 | 16.6 |
| Multifect ® CX12L | 20.11 | 0.00 | 6.6 |
| Novozyme-188 | 0.75 | 2.92 | 4.2 |

TABLE 2

End of saccharification hydrolysate properties for MD07#3

| | |
|---|---|
| Monomer Glucose (g/L) | 72.50 |
| Oligomer Glucose (g/L) | 20.62 |
| Monomer Xylose (g/L) | 40.20 |
| Oligomer Xylose (g/L) | 43.74 |
| Monomer Arabinose (g/L) | 4.11 |
| Oligomer Arabinose (g/L) | 7.94 |
| Solids content (wt %) | 22.4% |

Cob Hydrolysate FRF13
Pretreatment

Corn cob hydrolysate was prepared first by dilute ammonia pretreatment of ground corn cob using low ammonia methods described in U.S. Pat. No. 7,932,063. A horizontal Littleford Day 130 L reactor vessel containing a jacket for passing steam around the body of the vessel (Littleford Day, Inc., Florence, Ky.) was used for pretreatment to generate pretreated cob named SSL34. The vessel was loaded with cob from seed corn processing to reach 46 v % reactor fill on a wet cob basis (51 lbs). The cob had been reduced to less than 1 mm in size using a large micropulverizer (Model #1SH, Serial #10019; Pulverizing Machinery Co., Summit, N.J.) with a 1.0 mm screen. A scoop of dry ice was added as needed to the cob before grinding to prevent the equipment from heating up. The main drive of the micropulverizer is a 5 h.p. motor, with a maximum rotor speed of 9,600 RPM. It has six rotating hammers, a shell, and is lined with opposing impact edges.

The cob had a wet loose bulk density of 0.385 g/cm$^3$ and 7.4 wt % moisture. Vacuum was applied to the vessel to reach 0.1 atm prior to introduction of a 28.9 wt % ammonium hydroxide solution (9.8 lbs) and water (17.9 lbs) near the top of the vessel to give 6 wt % $NH_3$ relative to dry weight biomass and 60 wt % solids inside the vessel. A second and third pretreatment batch, named SSL35 and SSL36, were performed in the same manner to generate enough material for the subsequent saccharification. In all batches, the reactor agitator was set to 70 rpm and steam was passed through the jacket of the vessel. When the vessel reached an internal temperature of 80° C. steam was introduced near the top of the vessel to raise the internal vessel temperature to 145° C. This temperature was held for 20 minutes. At 15 minutes of this hold-up time the steam flow through the jacket was stopped. At the end of pretreatment, the reactor was depressurized through a vent condenser to reach atmospheric pressure. Vacuum (approximately to less than 1 atm) was subsequently applied for 15 minutes to lower the temperature to less than 60° C. and remove additional ammonia and water from the pretreated cob prior to opening the bottom valve of the vessel and recovering the pretreated biomass. Final wt % of solids for pretreated cob batches SSL34, SSL35, and SSL36 was 67.4%, 66.2%, and 68.0%, respectively.

Saccharification

A hydrolysate (FRF13) was generated in a 200 L fermenter using a mixture of the pretreated corn cobs from SSL34, SSL 35 and SSL36 preparations by saccharifying with the H3A protein described above. A water heel (120.0 kg) was added to the fermenter and sterilized with jacket heat to 121° C., held for 20 minutes. The water was cooled to 47° C. and the pretreated cob mixture was added through a port on the top of the tank; 20.0 kg were added at this time. The pH was adjusted to 5.3 with 1N $H_2SO_4$ and the enzyme preparation was added. The enzyme dosage was 4.53 kg, which was equivalent to 14 mg of protein per g of glucan+xylan in the total cob to be added to the reactor. Over the following 12 hours, four additions of 15.0 kg cob were made to the reactor, every three hours, with the pH adjusted to 5.3 with 1N $H_2SO_4$ after each addition. The target solids loading for this run was 25 wt %. The fermenter was controlled at 47° C. and pH 5.3 for approximately 72 hours. At the end of this time period, 20 liters was drawn off for use in these experiments, and the remaining contents of the vessel were fermented. A sample of the hydrolysate was analyzed and the remainder was stored refrigerated until use. The results of the sample analysis are shown in Table 3.

TABLE 3

End of saccharification hydrolysate properties for FRF13

| | |
|---|---|
| Monomer Glucose (g/L) | 49.20 |
| Oligomer Glucose (g/L) | 20.45 |
| Monomer Xylose (g/L) | 54.97 |
| Oligomer Xylose (g/L) | 27.24 |
| Monomer Arabinose (g/L) | 5.92 |
| Oligomer Arabinose (g/L) | 4.58 |
| Solids content (wt %) | 24.1% |

Example 1

Tolerance of Z. mobilis to Hop Acids

Z. mobilis strain ZW705 (described in General Methods) inoculum was prepared by reviving 2 mL of OD~10 frozen stock in 35 mL of MRM3G6 medium (10 g/L BBL yeast extract, 2 g/L $KH_2PO_4$, 1 g/L $MgSO_4*7H_2O$, 60 g/L glucose, pH 5.5) at 33° C. for ~8 hr. This culture was used to inoculate tubes containing clarified MD07#3 hydrolysate (see General Methods) supplemented with 2 g/L yeast extract and various hop acids preparations (see Table 4) at a 20% (final volume) inoculation rate, producing an initial OD of ~0.5. LactoStab® and IsoStab® (BetaTec, Hop Products Inc., John I. Haas, Inc., Washington, D.C.) were included at 100 ppm or 500 ppm. LactoStab® is about 9% hop bitter acids and IsoStab® is about 30% iso-alpha acid, making the actual concentrations used about 9 or about 45 ppm of hop bitter acids for the LactoStab® experiments and about 30 or about 150 ppm of iso-alpha acids for the IsoStab® experiments. Beta Bio 45% (Hopsteiner®, S.S. Steiner, Inc., New York, N.Y.) was included at 10 ppm or 50 ppm. Beta Bio 45% is 45% natural hop beta-acids, making the actual beta acid concentrations 4.5 or 22.5 ppm. Hopsteiner® Iso-Extract-30%, Tetra Iso-Extract, and Hexa Iso-Extract were included at 100 ppm or 500 ppm. Hopsteiner® Iso-Extract-30% is a 30% aqueous solution of the potassium salts of iso-alpha-acids produced from $CO_2$ hop extract, making the actual iso-alpha acid concentration 30 or 150 ppm. Hopsteiner® Tetra Iso-Extract is a 9.0% (w/w) aqueous solution of potassium salts of tetrahydroiso-alpha-acids produced from $CO_2$ hop extract. Thus 100 ppm of Tetra Iso-Extract is 9 ppm tetrahydroiso-alpha acid and 500 ppm of Tetra Iso-Extract is 45 ppm tetrahydroiso-alpha acid. Hopsteiner® Hexa Iso-Extract is a 9% (w/w) aqueous solution of potassium salts of hexahydroiso-alpha-acids and 1% of tetrahydroiso-alpha-acids produced from $CO_2$ hop extract. Thus 100 ppm of Hexa Iso-Extract is 9 ppm hexahydroiso-alpha acid and 1 ppm tetrahydroiso-alpha acid, and 50 ppm of Hexa Iso-Extract is 45 ppm hexahydroiso-alpha acid and 5 ppm tetrahydroiso-alpha acid.

Figure 2:
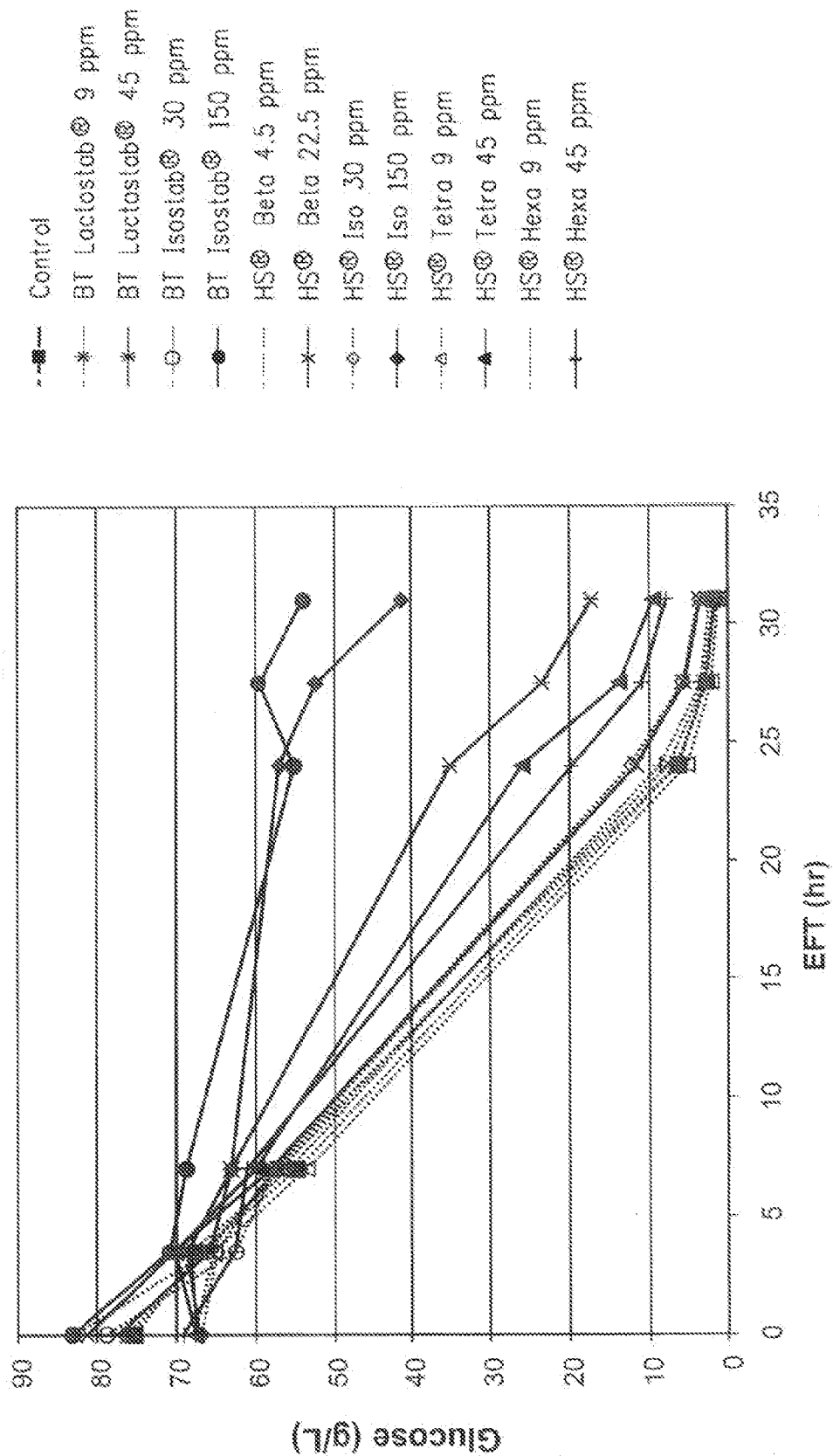
FIG. 2 is a graph showing glucose utilization by ZW705 cells grown in hydrolysate medium containing different amounts of hop acids in various commercial preparations, as marked, with full preparation names given in Example 1. HS®: Hopsteiner®, BT: BetaTec.

A control culture included no hop acid. The tubes were maintained at 33° C. with shaking for 32 hours, while glucose consumption was followed using a YSI7100 Multiparameter Bioanalytical System (YSI Life Sciences, Yellow Springs, Ohio) that was calibrated for glucose. As shown in FIG. 2, glucose utilization by ZW705 was similar to utilization in the control culture for cultures containing the lower amount of each hop acid preparation. There was less glucose utilization in medium containing the higher amount of each type of hop acid preparation.

TABLE 4

Hop acids in commercial hop acid preparations

| Product | Type of hop acids | ppm of hop acids tested |
|---|---|---|
| LactoStab™ | bitter acids | 9, 45 |
| IsoStab™ | iso-alpha acids | 30, 150 |
| Beta Bio 45% | natural beta-acids | 4.5, 22.5 |
| Iso-Extract-30%, | iso-alpha acids | 30, 150 |
| Tetra Iso-Extract | tetrahydroiso-alpha-acids | 9, 45 |
| Hexa Iso-Extract | hexahydroiso-alpha-acids + tetrahydroiso-alpha-acids; 9:1 | 9 + 1*, 45 + 5 |

*amount of hexahydroiso-alpha-acids + amount of tetrahydroiso-alpha-acids

Example 2

Effect of Hop Acids on Controlling Contamination in Z. mobilis Seed Medium

Z. mobilis strain ZW705 inoculum was prepared as described in Example 1, growing to OD of about 2. Lactobacillus plantarum strain ATCC 8014 inoculum was prepared by inoculating MRS medium with an individual colony and allowing growth at 33° C. for 8 hr, at which point the OD was about 1.0.

Seed medium (10 g/L Amberex695 yeast extract, 2 g/L $KH_2PO_4$, 5 g/L $MgSO_4 \cdot 7H_2O$, 10 mM sorbitol, 150 g/L glucose, pH 5.5) was prepared and sterilized by autoclaving (121° C., 30 min). To one sample of the seed medium 25 ppm of Hopsteiner® Iso-Extract-30% (7.5 ppm iso-alpha acid) was added (F1075) and no hop acids were added to the other sample (control; F1074). Each sample was inoculated with a mixture of Z. mobilis ZW705 (to OD of 0.05) and L. plantarum ATCC 8014 (to OD of 0.0005) and fermented at 33° C. and pH 5.5 using 4 N $NH_4OH$ for pH control.

Figure 3A:
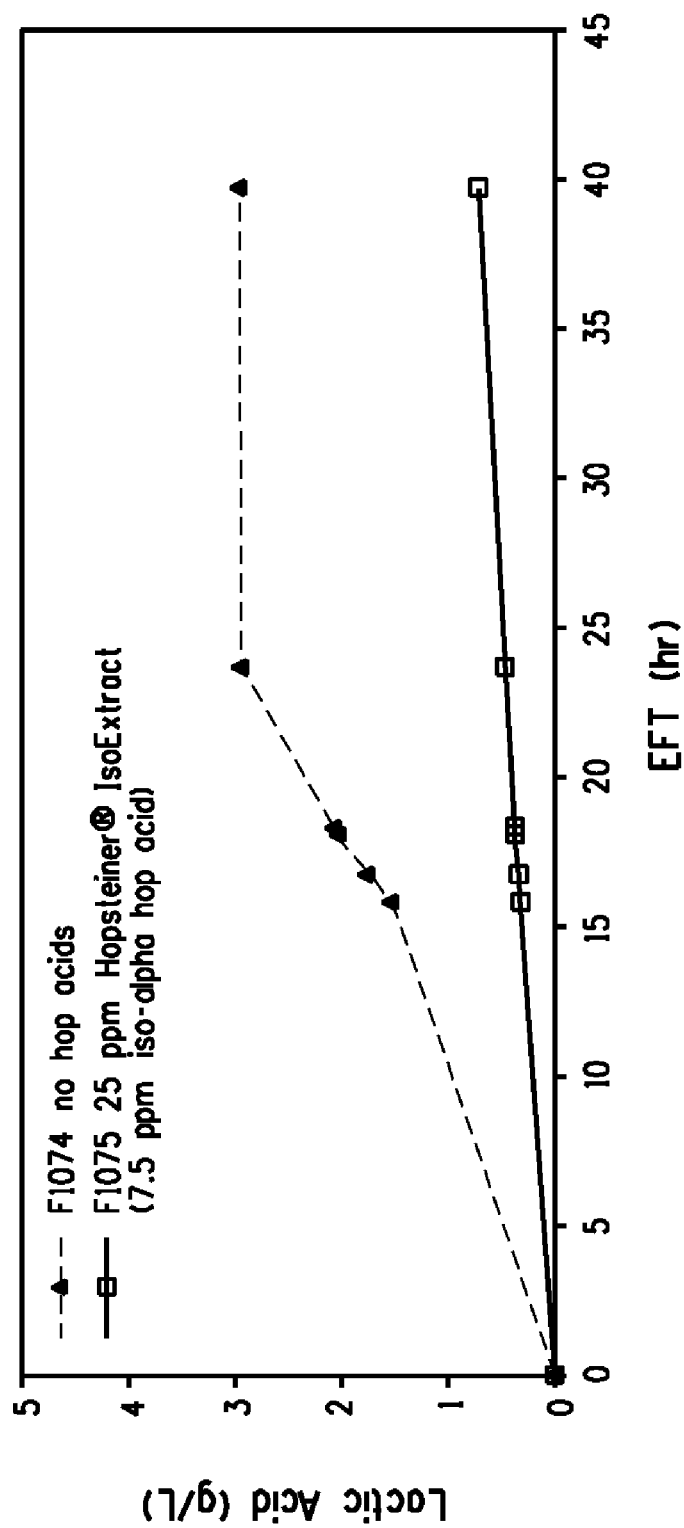
FIG. 3 shows graphs of lactic acid concentration (A) and ethanol concentration (B) in seed medium without hop acids or with 25 ppm of Hopsteiner® Iso-Extract-30% that was inoculated with a 1:100 ratio of *Lactobacillus plantarum*:*Z. mobilis* strain ZW705.
Figure 3B:
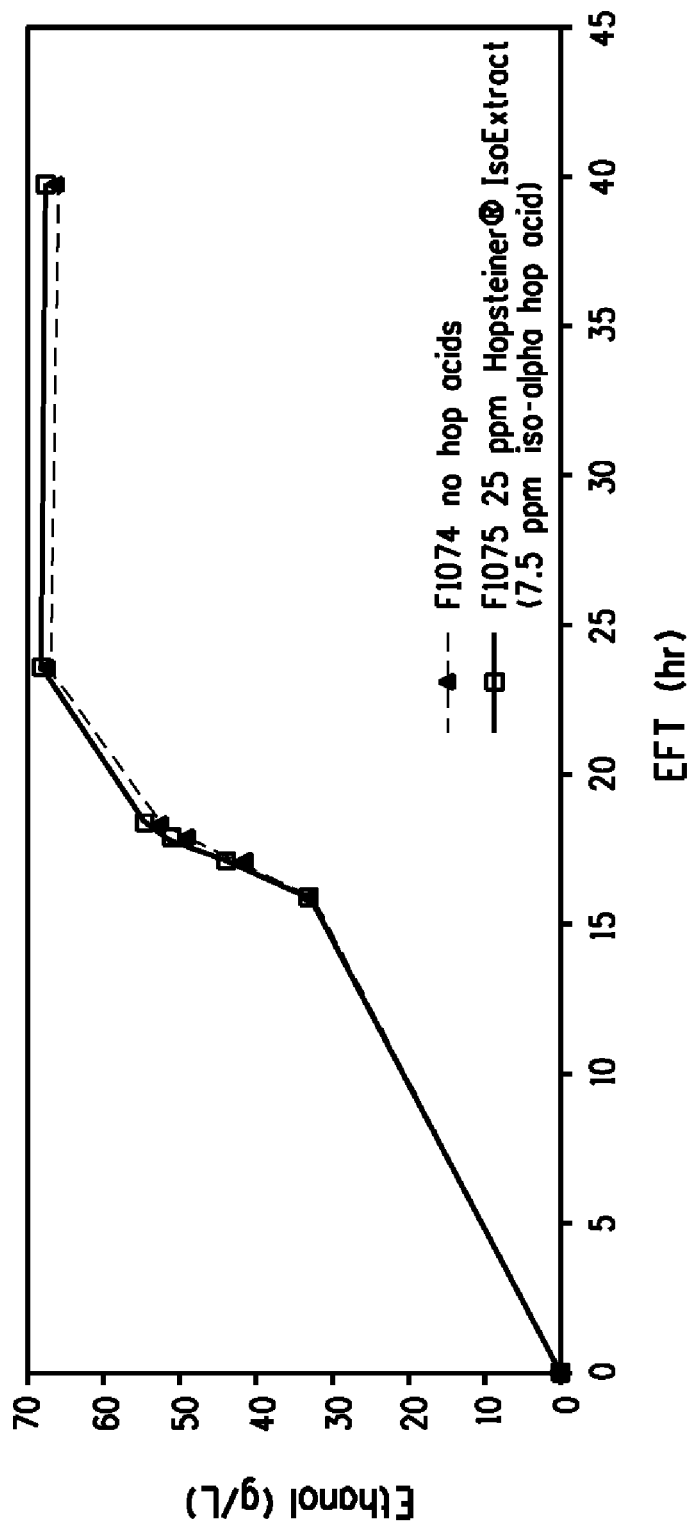

Medium samples were assayed periodically during fermentation by HPLC (Aminex 87H column, 0.01N $H_2SO_4$, 0.6 mL/min) and results are shown in FIGS. 3A and B. In the culture lacking hop acids (sample F1074), after 18.0 hr of fermentation, 2.1 g/L of lactic acid and 52.1 g/L of ethanol had formed. After 23.8 hr of fermentation, 2.9 g/L of lactic acid and 67.6 g/L of ethanol had formed. In the culture with 25 ppm of Hopsteiner® Iso-Extract added to the medium (sample F1075), 0.36 g/L of lactic acid was produced at 18.0 hr and 0.45 g/L at 23.8 hr, illustrating the effectiveness of a 25 ppm Hopsteiner® Iso-Extract dose in reducing L. plantarum growth, as evidenced by a reduced concentration of lactic acid. Ethanol concentration at 23.8 hr was 68.3 g/L in the culture dosed with Hopsteiner® Iso-Extract vs. 67.6 in the undosed culture, indicating lack of detrimental effect for Z. mobilis production of ethanol.

Example 3

Figure 4A:
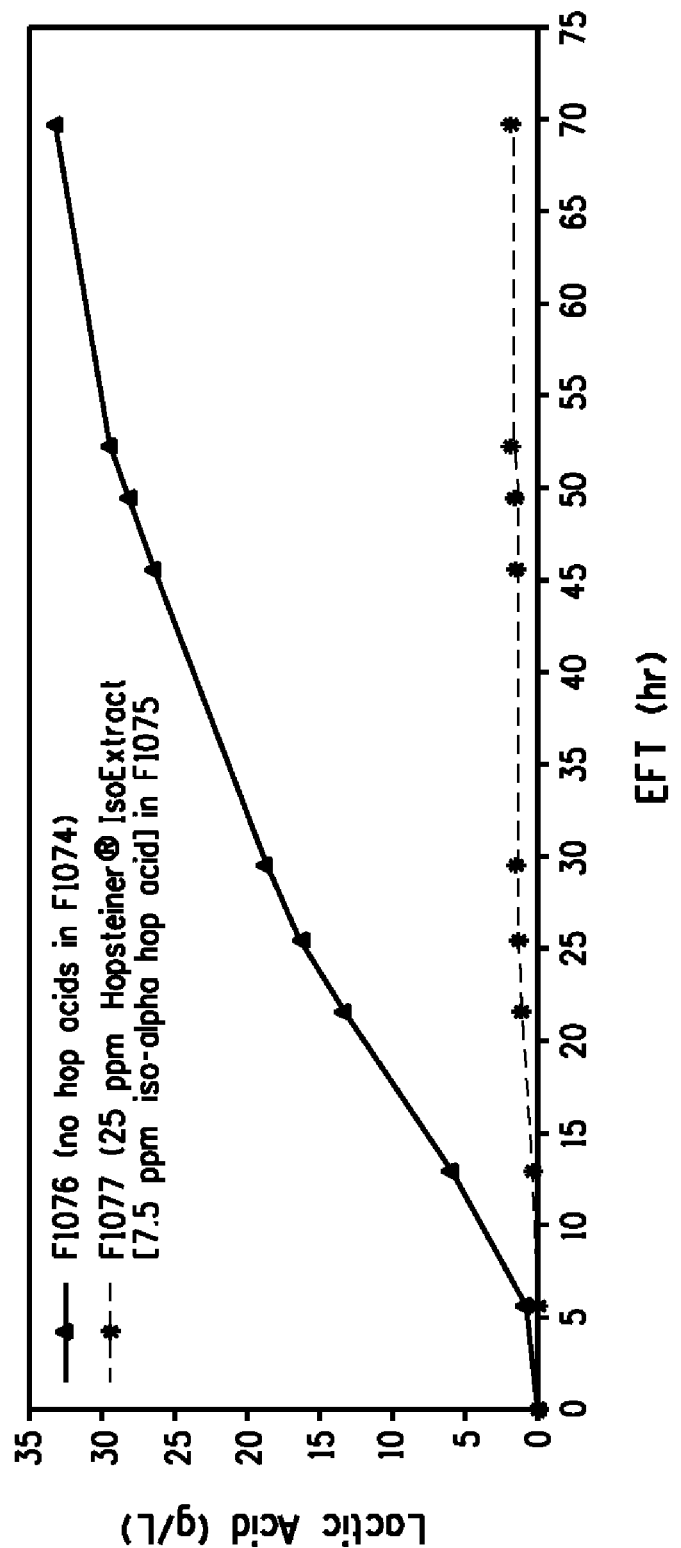
FIG. 4 shows graphs of lactic acid concentration (A) and ethanol concentration (B) in hydrolysate medium inoculated with seed culture initially inoculated with a 1:100 ratio of *Lactobacillus plantarum:Z. mobilis* strain ZW705 and grown without hop acids; or seed culture initially inoculated with a 1:100 ratio of *Lactobacillus plantarum:Z. mobilis* strain ZW705 and grown with 25 ppm of Hopsteiner® Iso-Extract-30%.
Figure 4B:
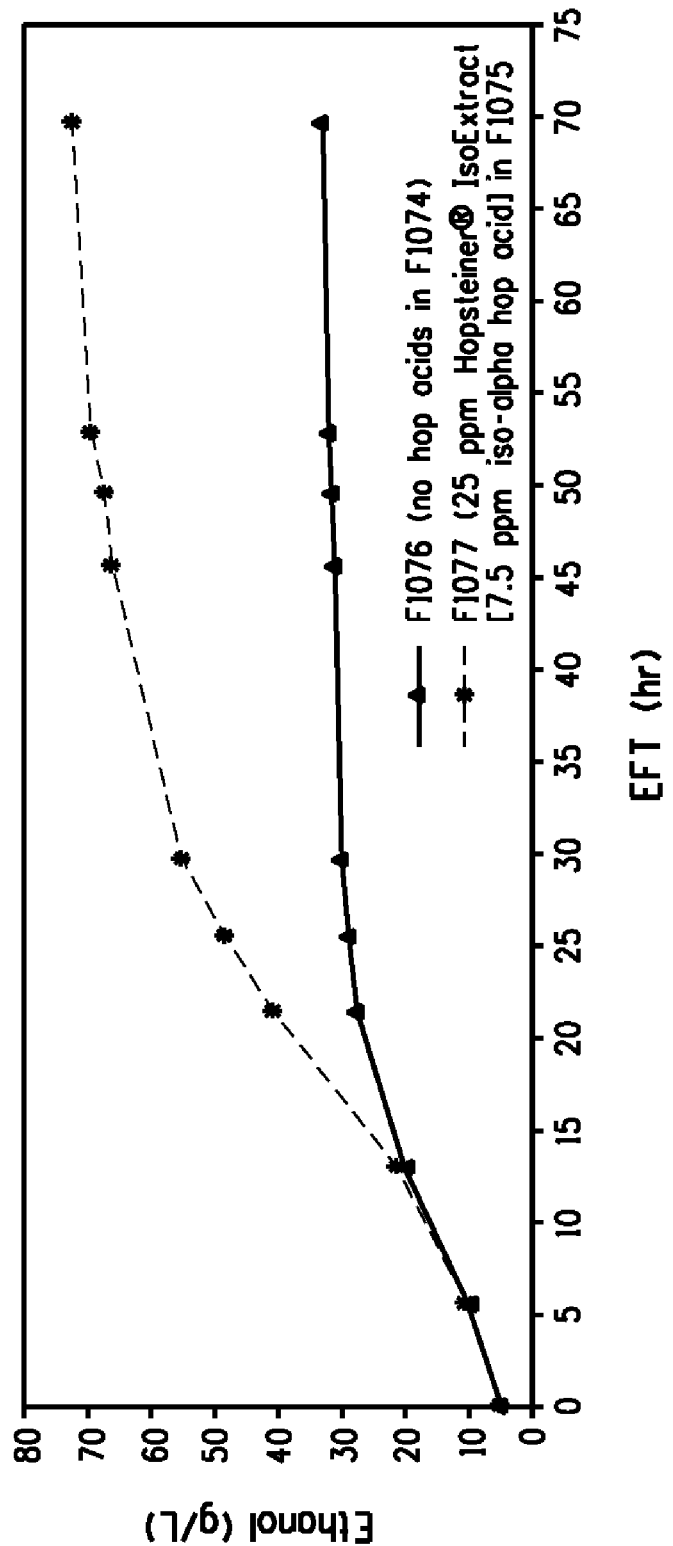
Figure 5A:
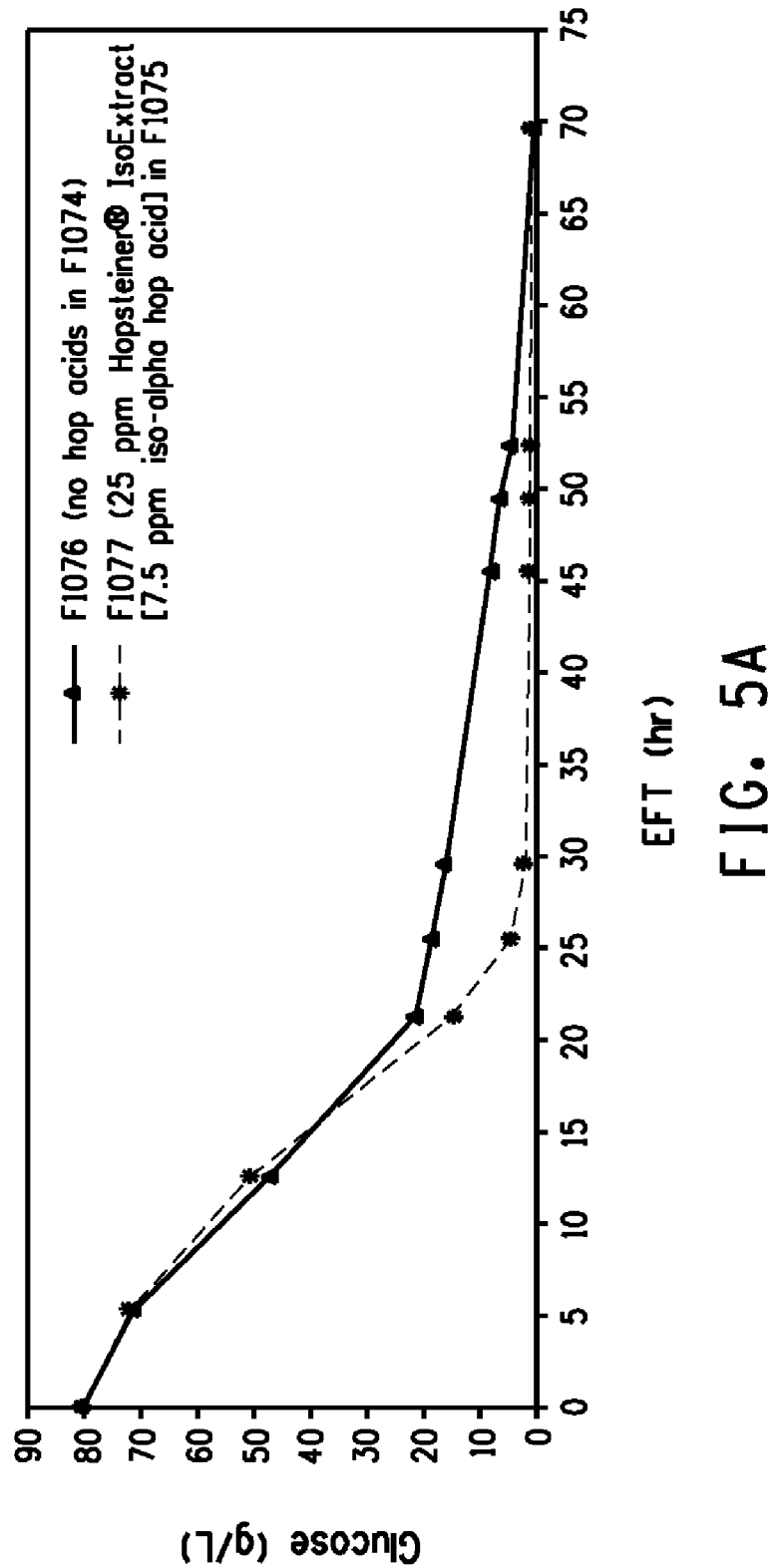
FIG. 5 shows graphs of glucose utilization (A) and xylose utilization (B) in hydrolysate medium inoculated with a seed culture initially inoculated with a 1:100 ratio of *Lactobacillus plantarum:Z. mobilis* strain ZW705 and grown without hop acids, or seed culture initially inoculated with a 1:100 ratio of *Lactobacillus plantarum:Z. mobilis* strain ZW705 and grown with 25 ppm of Hopsteiner® Iso-Extract-30%.
Figure 5B:
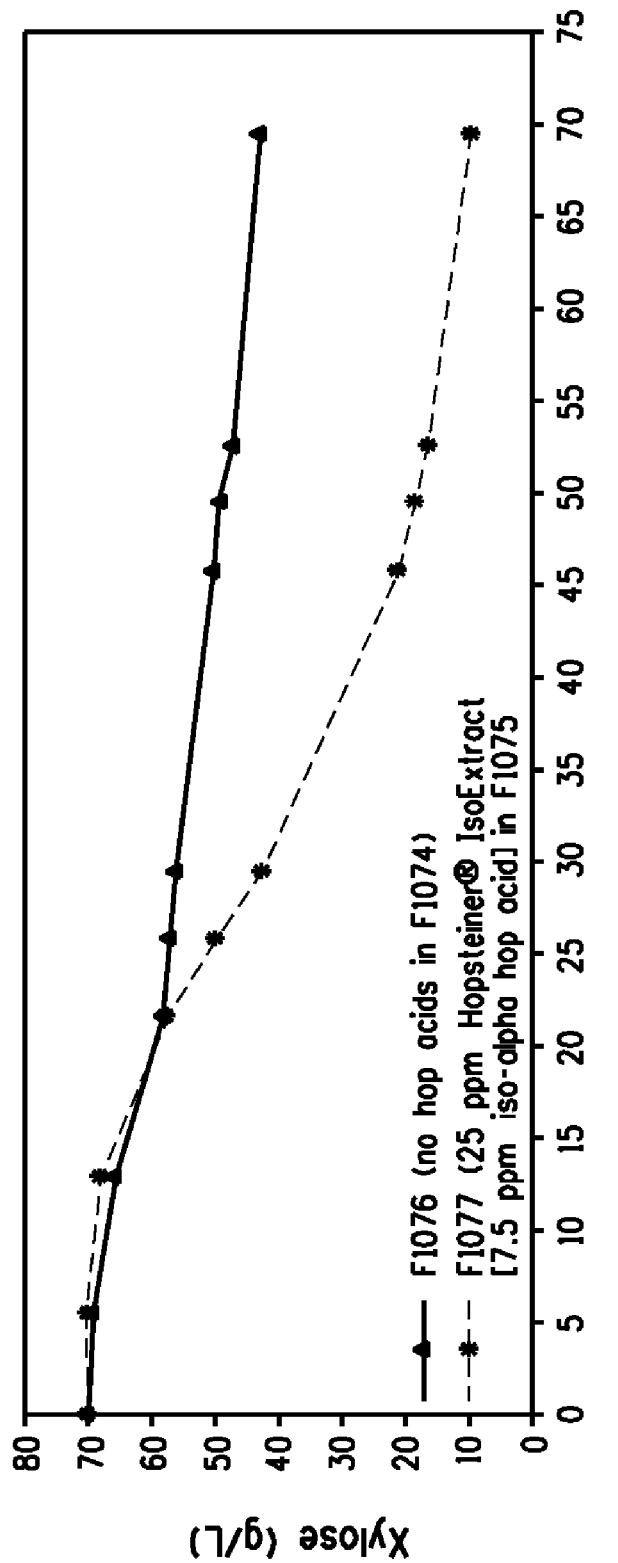

Effect of Using Hop Acids-Treated Z. mobilis Seed as Hydrolysate Medium Inoculum A portion of the culture lacking hop acids from Example 2 (F1074) that was taken at EFT=18.0 hr was used as a seed culture to inoculate FRF13 cob hydrolysate (described in General Methods) medium (adjusted to pH 5.8, +10 mM sorbitol) at 10 vol % (final volume), which was fermented at 33° C. (reduced to 30° C. at EFT=22 hr) and pH 5.8 (adjusted with 4 N NaOH). Medium samples were assayed periodically during fermentation and results are shown in FIG. 4 (run F1076). After 45.8 hr of fermentation, 26.3 g/L of lactic acid (FIG. 4A) and 31.4 g/L of ethanol (FIG. 4B) had formed. Also a significant amount of xylose was left unconsumed (FIG. 5B).

In a parallel experiment a portion of the culture with 25 ppm of Hopsteiner® Iso-Extract-30% (Example 2; F1075) taken at 18.0 hr was used as the seed culture for fermentation using the same conditions. Medium samples were assayed periodically during fermentation and results are shown in FIG. 4 (run F1077). After 45.7 hr of fermentation, 66.6 g/L of ethanol had formed (FIG. 4B), with only 1.3 g/L of lactic acid (FIG. 4A), showing that a small dose of Hopsteiner® Iso-Extract-30%, introduced into an intentionally-contaminated seed, was sufficient to prevent contamination of seed-inoculated hydrolysate fermentation. In this run glucose was utilized more rapidly (FIG. 5(A)) and xylose was utilized more completely (FIG. 5(B)) than in run F1076. The inclusion of hop acids in the seed allowed better glucose and xylose utilization in the cob hydroloysate medium, and increased production of ethanol.

Example 4

Hop Acid Effectiveness in Z. mobilis Hydrolysate

To determine the dose of hop acids in the Hopsteiner® Iso-Extract-30% that is required to prevent lactic acid formation in hydrolysate medium, a portion of the intentionally-contaminated culture grown without hop acids from Example 2 (F1074) taken at EFT=18.0 hr was used as a seed culture to inoculate FRF13 cob hydrolysate (described in General Methods) medium (adjusted to pH 5.8, +10 mM sorbitol) at 10 vol % (final volume). To one culture (run F1078) 25 ppm of Hopsteiner® Iso-Extract-30% (7.5 ppm iso-alpha acids) was included and no hop acids preparation was added to another culture (run F1076). The cultures were then fermented at 33° C. (reduced to 30° C. at EFT=21 hr) and pH 5.8 (adjusted with 4 N NaOH).

Figure 6A:
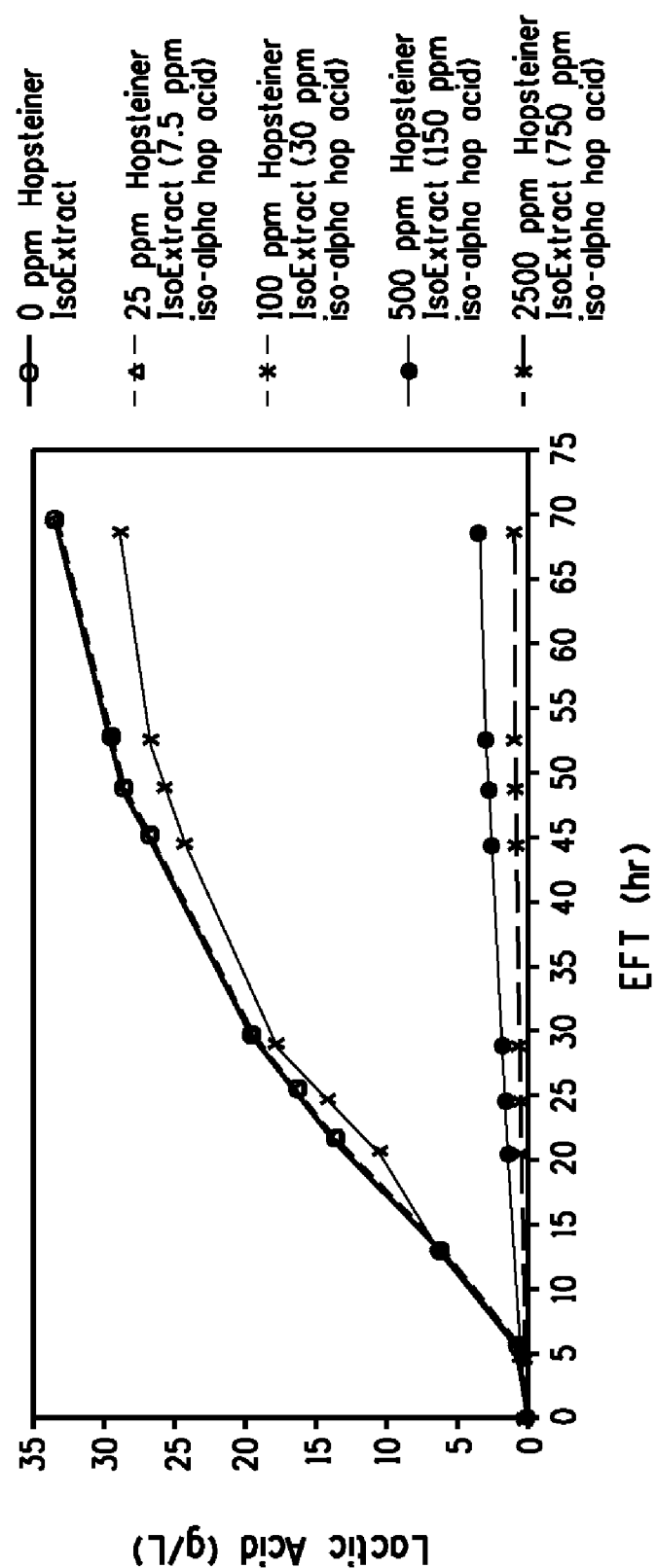
FIG. 6 shows graphs of lactic acid concentration (A) and ethanol concentration (B) in hydrolysate medium inoculated with a seed culture initially inoculated with a 1:100 ratio of *Lactobacillus plantarum:Z. mobilis* strain ZW705 and grown without hop acids, and fermented in the presence of different amounts of Hopsteiner® Iso-Extract-30%.
Figure 6B:
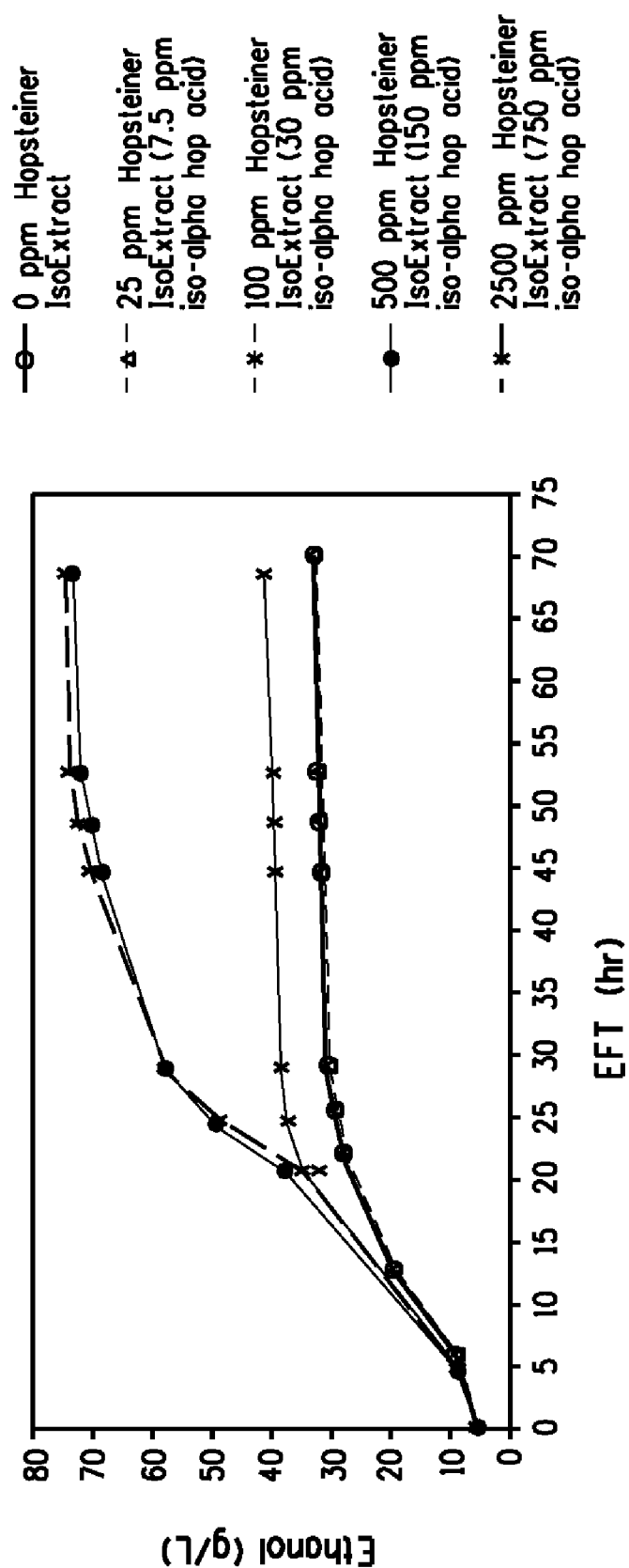

To explore higher concentrations of Hopsteiner® Iso-Extract-30%, a seed culture similar to F1074 was produced and used to inoculate FRF13 cob hydrolysate in a similar manner as described above, in the presence of 100, 500, or 2500 ppm Hopsteiner® Iso-Extract-30% (30, 150, or 750 ppm iso-alpha acids; runs F1084-1086, respectively). Medium samples were assayed periodically during fermentation and results are shown in FIG. 6. Large quantities (>20 g/L at 44.7 hr) of lactic acid were produced in medium containing 0, 25, and 100 ppm Hopsteiner® Iso-Extract-30% (equivalent to 0, 7.5, 30 ppm of iso-alpha acids, respectively). Including 500 ppm Hopsteiner® Iso-Extract-30% (150 ppm iso-alpha acids) reduced lactic acid formation to 2.5 g/L at 44.7 hr. Including 2500 ppm Hopsteiner® Iso-Extract (750 ppm iso-alpha acids) maintained lactic acid concentration at less than 1 g/L, illustrating the need for higher concentrations of hop acid in controlling contaminating organisms in hydrolysate fermentation. Ethanol concentration at 48.7 hr in the runs containing 500 or 2500 ppm Hopsteiner® Iso-Extract was above 70 g/L, while the runs that received lower doses had ethanol concentrations <40 g/L at the same time (FIG. 6(B)), further illustrating the requirement for higher concentrations of hop acids in combating contamination and improving ethanol production in contaminated batches.

What is claimed is:

1. A fermentation broth composition comprising:
   a) fermentation medium comprising a cellulosic biomass hydrolysate; hop acids at a concentration of greater than 500 ppm; and a growing population of Zymomonas cells.

2. The fermentation broth of claim 1 wherein the concentration of lactic acid is less than about 5 g/L.

3. A method for controlling bacterial contamination in a fermentation using a *Zymomonas* cell biocatalyst comprising:
   a) providing a fermentation medium comprising cellulosic biomass hydrolysate;
   b) adding hop acids to the fermentation medium to a concentration of greater than 500 ppm;
   c) adding to the fermentation medium an inoculum of *Zymomonas* cells, thereby producing a fermentation broth; and
   d) maintaining the fermentation broth under conditions suitable for growth of the *Zymomonas* cells;
whereby bacterial contamination is controlled.

4. The method of claim 3 wherein the *Zymomonas* cells produce ethanol in the fermentation broth.

5. A method for producing ethanol comprising:
   a) providing a fermentation medium comprising cellulosic hydrolysate;
   b) adding to the fermentation medium an inoculum of *Zymomonas* cells grown in the presence of hop acids, producing a fermentation broth wherein the concentration of hops acids is greater than 500 ppm; and
   c) maintaining the fermentation broth under conditions suitable for growth of the *Zymomonas* cells and production of ethanol by the *Zymomonas* cells;
   wherein no hop acids are added to the fermentation medium separately from the inoculum of (b) and wherein ethanol is produced.

* * * * *